United States Patent [19]

Willison

[11] Patent Number: 4,720,192

[45] Date of Patent: Jan. 19, 1988

[54] GLASS BOTTLE INSPECTION UNIT

[75] Inventor: Beverly G. Willison, Akron, Ohio

[73] Assignee: FECO Engineered Systems, Inc., Cleveland, Ohio

[21] Appl. No.: 723,806

[22] Filed: Apr. 16, 1985

[51] Int. Cl.$^4$ ............................................. G01N 21/00
[52] U.S. Cl. ................................... 356/240; 356/428; 209/526
[58] Field of Search ....................... 356/240, 427, 428; 250/223 B; 198/346, 346.2, 385; 209/522, 524, 528

[56] References Cited

U.S. PATENT DOCUMENTS

| | | | |
|---|---|---|---|
| 2,196,389 | 4/1940 | Fogg et al. | 356/240 X |
| 2,446,377 | 8/1948 | Marshall | 356/240 |
| 2,779,490 | 1/1957 | Clarke et al. | 198/346.2 |
| 3,356,853 | 12/1967 | Rottmann | 209/526 X |
| 4,483,615 | 11/1984 | Bieringer et al. | 209/526 X |

FOREIGN PATENT DOCUMENTS 2706915 8/1978 Fed. Rep. of Germany ...... 209/526

Primary Examiner—Eugene R. LaRoche
Assistant Examiner—Robert J. Pascal
Attorney, Agent, or Firm—Patrick J. Walsh

[57] ABSTRACT

A glass bottle inspection unit includes an endless conveyor having a series of spaced roller members defining therebetween grooves for receiving glass bottles for inspection. The conveyor member carries the bottles through an inspection station and means are provided for rotating the rollers and bottles several times as they move through the inspection station to facilitate inspection. An inspection unit module may be tilted between horizontal and vertical positions to facilitate viewing at the inspection station. Illumination is provided as an aid to visual inspection of the bottles.

5 Claims, 5 Drawing Figures

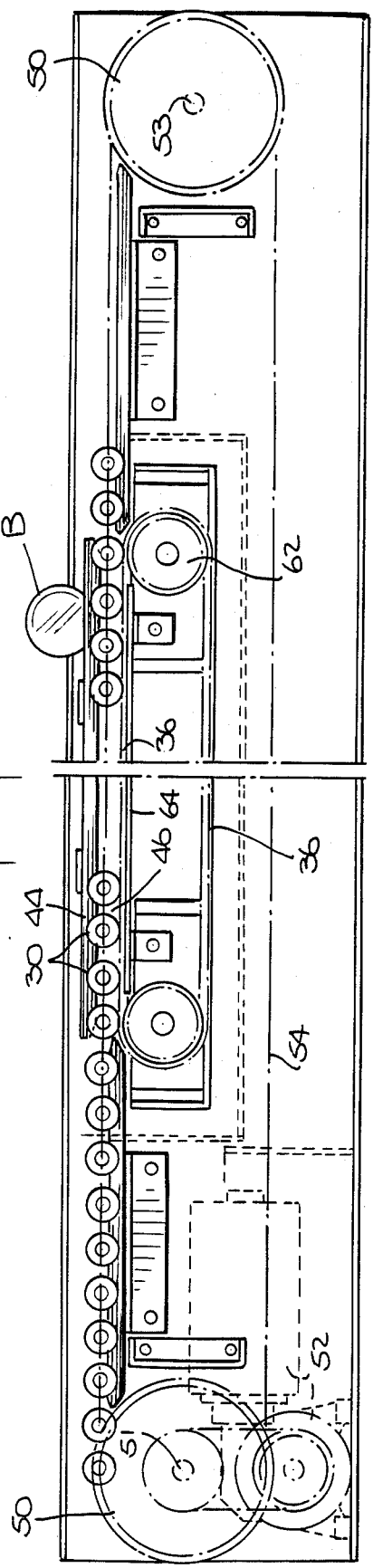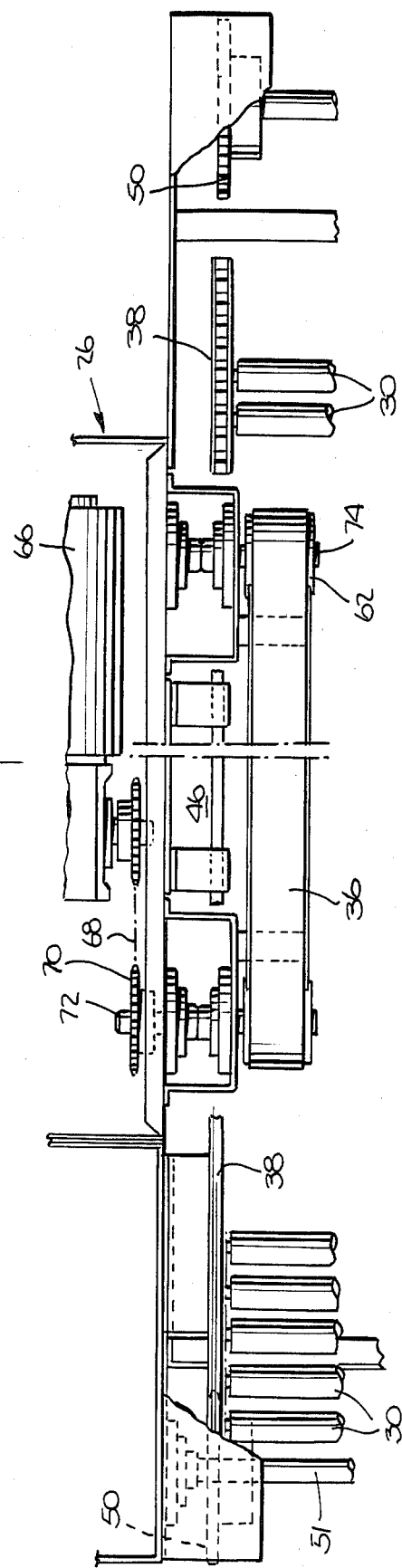

GLASS BOTTLE INSPECTION UNIT

BACKGROUND OF THE INVENTION

In packaging consumer products in bottles, particularly glass bottles, it is necessary to inspect the bottles prior to being filled with the consumer product at a packaging plant. Such inspections are necessary in order to remove from the packaging operation bottles having imperfections such as cracks, impurities, scratches, manufacturing flaws, and the like. At the present time inspection of bottles is done manually by inspectors who hold each bottle to a light source to inspect for imperfections. This manual system can be tolerated in packaging plants where filling equipment operates at relatively slow speeds. With increased speed of filling equipment such manual inspection procedures have become cumbersome and the need has arisen for a method and apparatus of inspection of bottles without the inspector handling each bottle for inspection.

SUMMARY OF THE INVENTION

According to the present invention there is provided an inspection unit for glass and other bottles permitting inspection of each bottle without handling by an inspector. According to the invention, bottles which are normally conveyed in an upright manner are conveyed into the inspection unit and are inclined and rotated as they pass an inspection station such that an inspector has a complete view of each bottle without removing the bottle from the conveying line, inspecting and replacing the bottle after inspection is complete. Additionally, the inspection may now be carried out under a transparent protective cover so that impurities are not introduced during the inspection procedure.

The inspector can then either manually, semiautomatically or automatically remove bottles which fail the inspection standards.

According to the invention the inspection unit is positioned in a convenient location in a production line and comprises an inlet conveyor for moving bottles from essentially an upright to a tilted or inclined orientation. The inspection unit has an endless conveyor member comprising a series of rollers spaced from one another and defining a plurality of grooves therebetween for receiving and conveying bottles. The rollers are carried by endless chain members and are free to rotate on their axes. A pressure belt moves on the underside of the roller conveyor for the purpose of engaging and rotating the rollers such that the bottles rotate as they pass through the inspection station. During inspection the bottles are either passed on to a filling station or are removed if an imperfection is detected.

OBJECTS OF THE INVENTION

Accordingly, it is an object of the invention to provide a glass bottle inspection unit in which bottles are inspected at high speeds compatible with high speed filling equipment.

Another object of the invention is to eliminate the manual handling of each bottle by an inspector for imperfections.

Another object of the invention is to provide a conveying system for moving and rotating the bottles through the inspection station for convenient examination by an inspector.

Other and further objects of the invention will occur to those skilled in the art upon employment of the invention in practice.

DESCRIPTION OF THE DRAWING

A preferred embodiment of the invention has been chosen for illustration and description and is shown in the accompanying drawing in which:

FIG. 4 is a side elevational view showing the conveying path and the conveying means for the glass bottle inspection unit together with a pressure belt for rotating roller conveyor members.

FIG. 5 is a fragmentary plan view of the glass bottle inspection unit particularly illustrating the arrangement for pressure belt and its drive units.

DETAILED DESCRIPTION OF THE INVENTION

Figure 1:
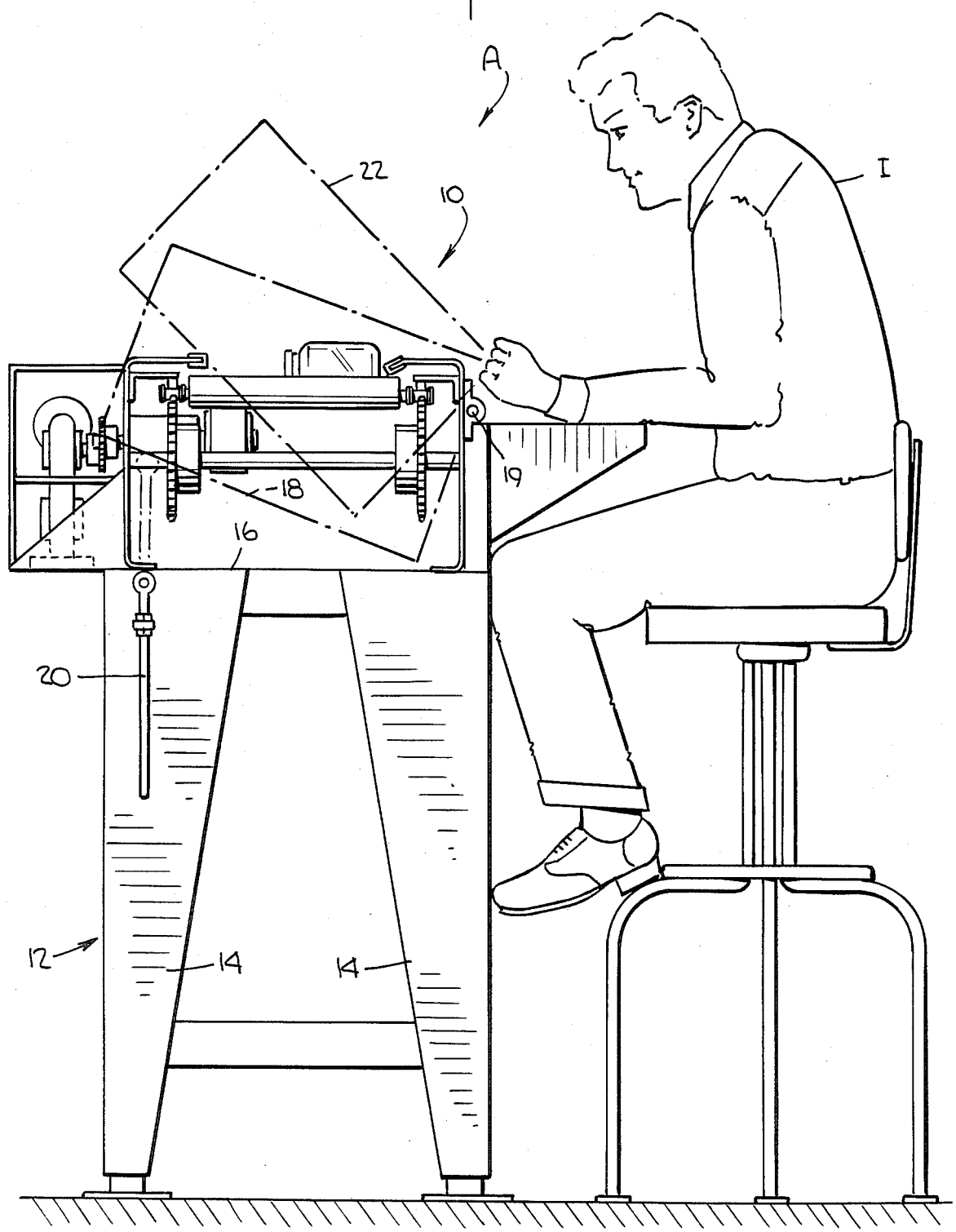
FIG. 1 is an end elevational view showing the general arrangement of the bottle inspection unit.
Figure 2:
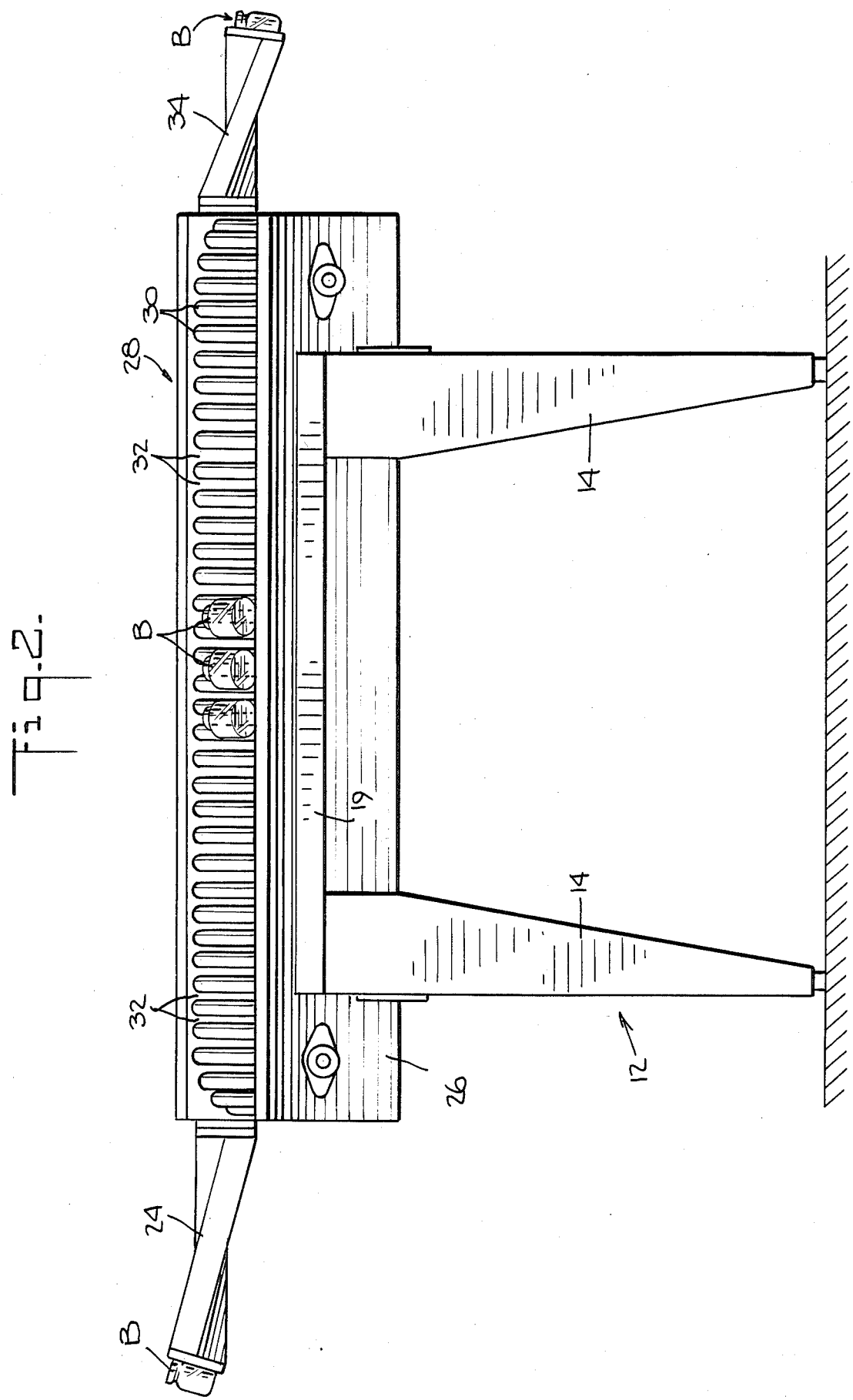
FIG. 2 is a front elevational view of the inspection side of the bottle inspection unit showing particularly the infeed conveying path, inspection station, and discharge conveying path of the inspection unit according to the present invention.

Referring now to the drawing and particularly to FIGS. 1 and 2, the bottle inspection unit 10 includes a suitable standard or machine frame 12 arranged along a glass bottle conveying path in a packing plant. The standard has upstanding leg members 14, a table member 16 and an inspection module 18 pivotally mounted at 19 to the standard. The inspection module 18 nominally is received and supported at the table surface 16. In ordinary operation it may be preferred to tilt the inspection module for convenient viewing and accordingly the inspection module is pivotally mounted to the machine frame by hinge 19. An adjustable arm 20 is fitted to the frame for supporting the inspection module in a convenient inclined position for viewing by an inspector I. If desired for improved sanitation, a protective cover 22 may be used to encase the inspection unit.

As shown in FIG. 2, upstanding bottles B are conveyed by a twist conveying track 24 for reception and movement through the inspection unit. The inspection unit comprises an elongated frame 26 pivotally mounted to the machine frame at hinge 19. An endless conveyor 28 defined by moving roller members 30 receives bottles from the infeed track. The arriving bottles are deposited in the spaces or grooves 32 between adjacent roller members and are carried through the inspection station to a discharge chute 34 which returns the bottles to a substantially vertical orientation.

Figure 3:
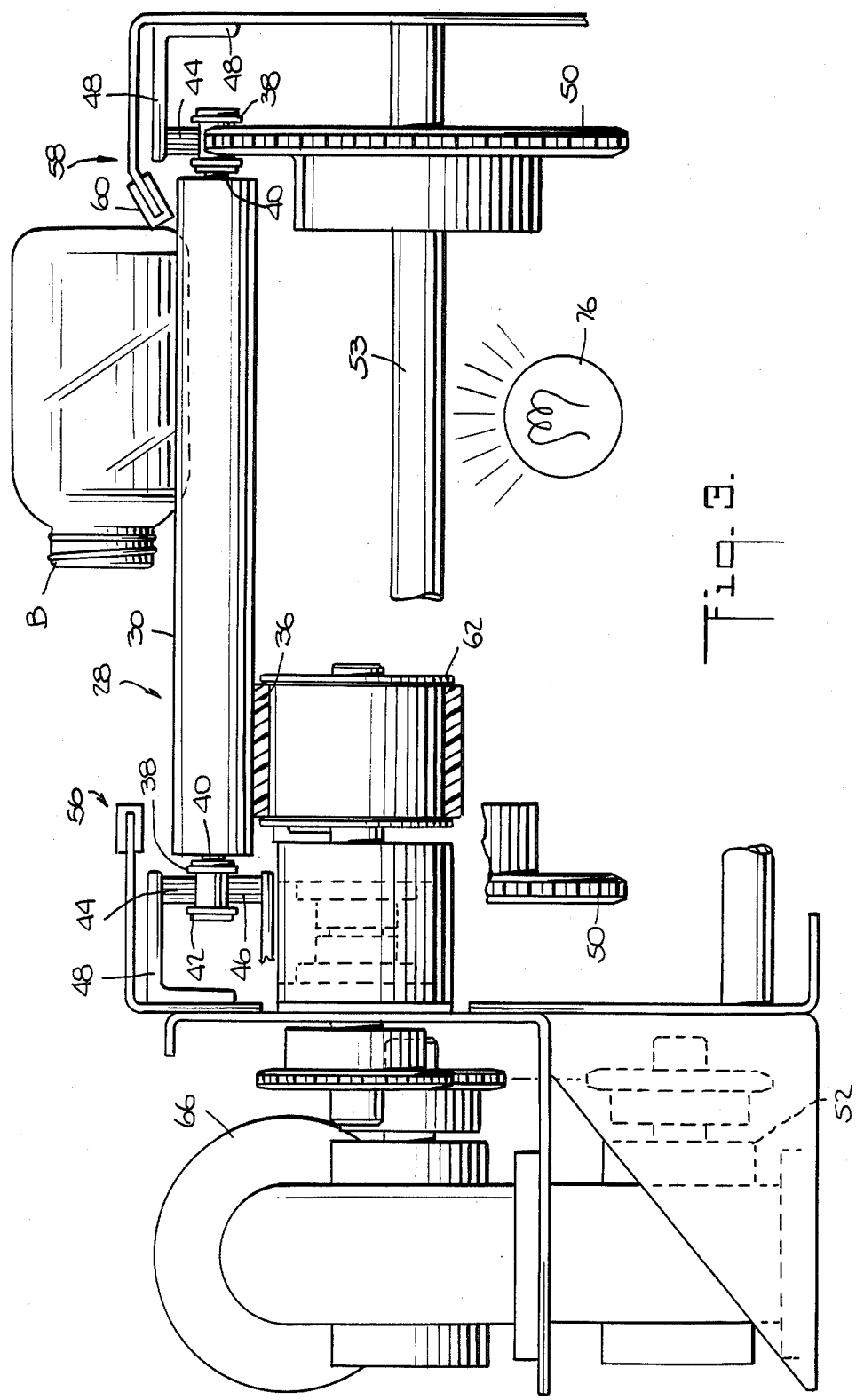
FIG. 3 is a fragmentary view in end elevation showing the driving and supporting arrangement for various components of the glass bottle inspection unit.

A pressure belt 36, FIGS. 3-5, rotates the roller members 30 during their passage through the conveying unit so that the inspector may view the entire outer surface of each glass bottle being conveyed. If a glass bottle is imperfect and does not meet inspection standards it may be removed by either manual or automatic means.

FIGS. 3, 4 and 5 illustrate the supporting and driving mechanism for the glass bottle inspection unit. The principal conveyor 28 for carrying bottles through the inspection unit comprises a series of rollers 30 mounted on spaced endless chain members 38 by suiable fittings 40 extending axially of each roller and received in the links 42 of chain members. As shown in FIG. 3, the spaced chain members ride along upper 44 and lower 46 support guides positioned on either side of the machine member within support channels 48.

The endless chain members are mounted over spaced sprockets 50 fitted to drive 51 and idler 53 shafts, and are driven by a suitable motor/gear drive mechanism 52 so that the roller conveyor traverses the path indicated by chain center line 54 in FIG. 4. The sprocket shafts and drive mechanims are supported by the inspection unit frame 26 in a conventional manner. A pair of guide members 56, 58 overlie and extend along the path of conveyance and define the lateral limits of the path travelled by the bottles. Preferably the guides have liners 60 made of low friction material for ease of conveyance.

The underside of the rollers as they pass through the inspection station are engaged by moving endless pressure belt member 36 which positively rotates roller members 30 such that a bottle B cradled between roller members will also rotate one or more and preferably three times as it passes through the inspection station. The pressure belt 36 is mounted over spaced wheel members 62, supported by plate member 64, and is driven by a suitable motor gearbox drive unit 66 through drive chain 68, sprocket 70, and drive 72 and idler 74 shafts supported by the frame 26.

Preferably, a source of illumination 76 (FIG. 3) is located in the interior of the inspection unit and will illuminate the containers passing along the inspection unit. A pair of spaced guide members 56, 58 line the conveying path and depending on the size of articles being conveyed tend to position the articles through the inspection zone. Typically the lower guide member engages the base portion of the bottles giving them a relatively uniform position passing through the inspection unit.

In operation the bottles move along spaced between adjacnet rollers on the roller conveyor 28. The moving belt 36 engages the underside of the rollers for the purpose of rotating the rollers and each bottle carried by adjacent rollers. An inspector therefore can view the bottles and arrange to have removed from the conveying system those bottles which do not meet inspection standards, such removal means being chosen from suitable equipment for such purposes. In practice, the actual line speed of the inspection will depend on bottle size and customer line speeds. The inspection unit is capable of handling up to 150 bottles per minute. Additionally, each bottle rotates approximately three times as it passes through the viewing zone of the unit.

While the invention has been described with particular reference to glass bottles it is to be understood that the inspection unit of the present invention can be used for inspection of a variety of generally cylindrical objects.

Having thus described our invention, I claim:

1. A glass bottle inspection unit comprising a conveyor for receiving and moving bottles through an inspection station, the conveyor having spaced carrier means defining an endless path, a plurality of generally cylindrical members supported for rotation at opposite ends by the spaced carrier members, the cylindrical members being spaced from each other and defining bottle receiving grooves therebetween, means for delivering bottles to the conveyor grooves for carriage through the inspection station, means for rotating the bottles as they move through the inspection station, and means for receiving bottles from the unit after being inspected.

2. A glass bottle inspection unit as defined in claim 1 in which the generally cylindrical members comprise rollers mounted for axial rotation to the spaced carrier means and which further includes a belt for engaging the rollers for rotating the rollers and bottles as they move through the inspection station.

3. A glass bottle inspection unit as defined in claim 2 in which the inspection unit is mounted to be tilted between horizontal and vertical positions for convenient viewing by an operator.

4. A glass bottle inspection unit as defiend in claim 2 which further includes a source of illumination beneath the rollers for illuminating the bottles as they pass through the inspection station.

5. A glass bottle inspection unit as defined in claim 2 in which each bottle revolves three times as it passes through the inspection unit.

* * * * *